United States Patent [19]

Stewart

[11] 4,098,272

[45] Jul. 4, 1978

[54] RESPIRATOR

[75] Inventor: Jeffrey L. Stewart, Brookfield, Conn.

[73] Assignee: Bio-Med Devices Inc., Stamford, Conn.

[21] Appl. No.: 616,660

[22] Filed: Sep. 25, 1975

[51] Int. Cl.² ............................................. A61M 16/00
[52] U.S. Cl. ............................. 128/145.8; 128/142.2; 137/624.14
[58] Field of Search .................... 128/145.5–145.8, 128/188; 137/624.14, 624.15

[56] References Cited

U.S. PATENT DOCUMENTS

| | | | |
|---|---|---|---|
| 3,446,207 | 5/1969 | Metivier | 128/145.8 |
| 3,730,180 | 5/1973 | Davison | 128/145.6 |
| 3,905,362 | 9/1975 | Eyrick et al. | 128/145.8 |
| 3,910,270 | 10/1975 | Stewart | 128/145.8 |
| 3,916,889 | 11/1975 | Russell | 128/145.8 |

*Primary Examiner*—Robert W. Michell
*Assistant Examiner*—Henry J. Recla
*Attorney, Agent, or Firm*—St. Onge, Steward, Johnston, Reens & Noe

[57] ABSTRACT

A respirator is described wherein a plurality of pneumatic bistable elements are employed in an automatically operated pneumatic circuit. A constant inspiratory to expiratory ratio pneumatic circuit is provided to simplify respirator control. A demand sensing circuit interrupts an oscillator to commence an inspiratory phase in response to pressure changes introduced in a patient gas supply circuit. A manual control is provided to enable manual dispensing of respiratory support. A pneumatic circuit is provided for generating an end inspiratory plateau period. During this period gas equilibration in different compartments of the lung is permitted and in addition a measurement of peak intraalveolar pressure is made.

10 Claims, 4 Drawing Figures

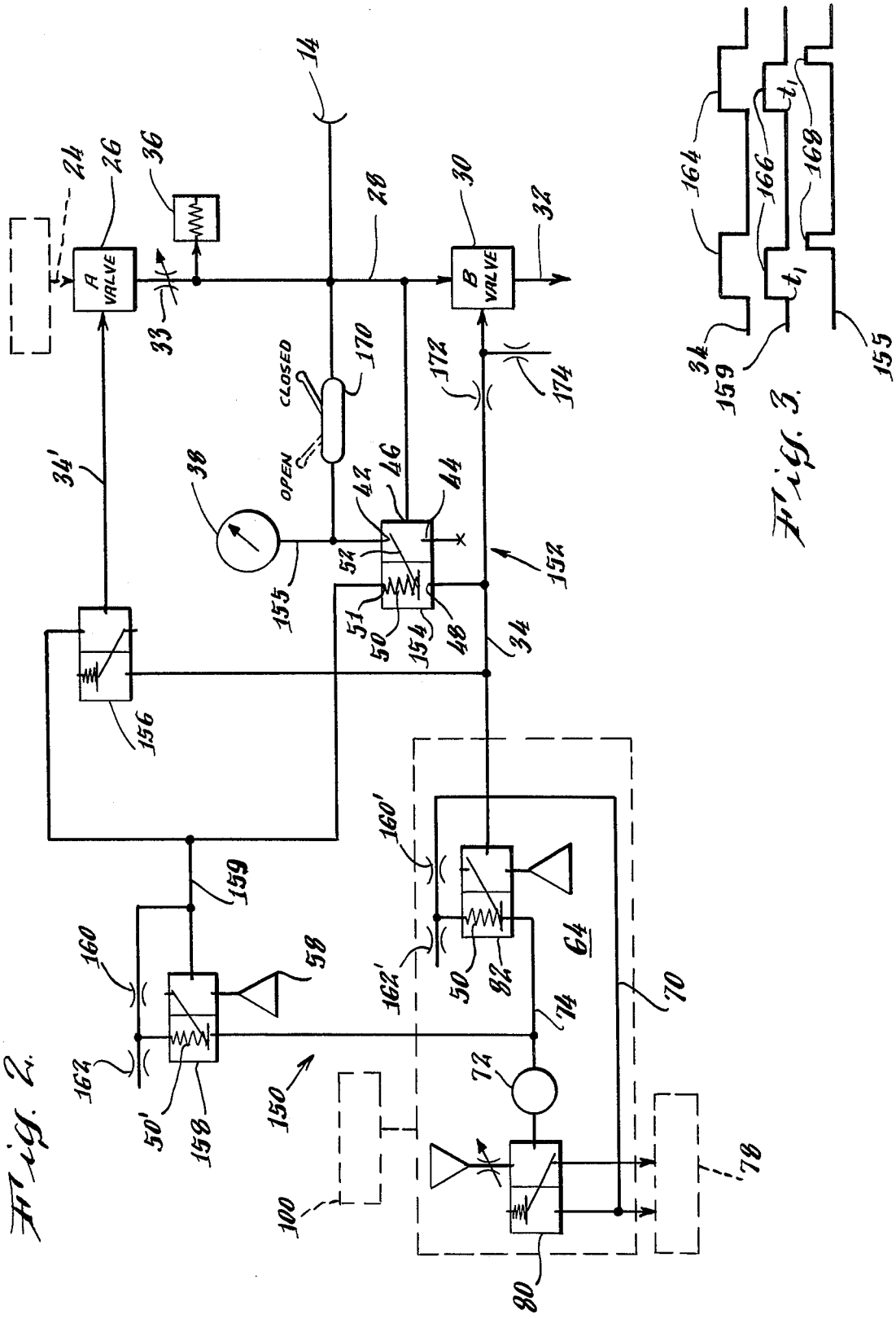

RESPIRATOR

REFERENCE TO PRIOR APPLICATION

Reference is made to two copending patent applications respectively for a Pediatric Respirator, filed on June 7, 1974 with Ser. No. 477,194, now U.S. Pat. No. 3,949,749 and for a Portable Volume Cycled Respirator filed Feb. 25, 1974 with Ser. No. 445,758, now U.S. Pat. No. 3,910,270 both having been filed by the same inventor as for this application and assigned to the same assignee as for this application.

FIELD OF THE INVENTION

This invention relates to a respirator generally and more specifically to a portable respirator of the pneumatic type capable of ventilating many types of patients.

BACKGROUND OF THE INVENTION

Respirators have been used for many years to aid the breathing cycles of patients in a variety of situations. Typically, a respirator may employ controls capable of regulating the supply of breathable gas to a patient mask during both inspiratory and expiratory phases.

In the U.S. patent to Sundblom et al. U.S. Pat. No. 3,669,108 a respirator is described to provide both volume and pressure breathing cycle control. In a volume cycled control, a predetermined volume of gas is supplied to a patient during a particular time period while in a pressure cycled control the inspiratory gas flow is terminated when a predetermined alveolar or airway pressure occurs.

In the Sundblom patent the illustrated respirator provides a variety of different operational conditions. For example, with one type of control one may automatically maintain a preset ratio of inspiratory time to expiratory time. Other controls permit an independent setting of the inspiratory time or tidal volume, manual override and a flow pattern adjustment to determine limits for the initial and terminal gas flows.

The automatic control over ratio of inspiratory time to expiratory time is achieved in the Sundblom patent respirator by allowing the pressure in a gas chamber to build up during the inspiratory cycle. The final gas pressure attained then becomes a function of the inspiratory time and the volume of gas stored during the inspiratory cycle. The final gas pressure attained then becomes a function of the inspiratory time and the volume of gas stored during this period is controllably discharged to set an expiratory time period.

SUMMARY OF THE INVENTION

With a respirator in accordance with the invention, a plurality of pneumatic bistable elements are employed to provide a compact respirator with a predetermined inspiratory to expiratory time ratio or vice versa. The bistable elements provide a compact respirator with a manual control and a demand circuit. The respirator has few controls and a construction which enables a low gas consumption for relatively long use in areas having a limited supply of gas.

With a pneumatic respirator in accordance with the invention, improved reliability is obtained by using a minimum of moving parts and employing a common pneumatic bistable element to provide a variety of logic functions.

With a pneumatic respirator in accordance with the invention, a measurement of alveolar or airway pressure at the end of an inspiratory phase may be conveniently measured and indicated.

It is, therefore, an object of the invention to provide a portable pneumatically controlled reliable respirator capable of ventilating patients under a variety of conditions with a convenient to operate and practical pneumatic circuit construction.

BRIEF DESCRIPTION OF DRAWINGS

These and other advantages and objects of the invention can be understood from the following description of several embodiments shown in the drawings wherein

FIG. 2 is a schematic representation of a pneumatic circuit for measuring alveolar pressure at the end of an inspiratory or breathing cycle;

FIG. 3 is a timing diagram of pneumatic pressure pulses generated in the pneumatic circuit of FIG. 2.

DESCRIPTION OF DRAWINGS

Figure 1:
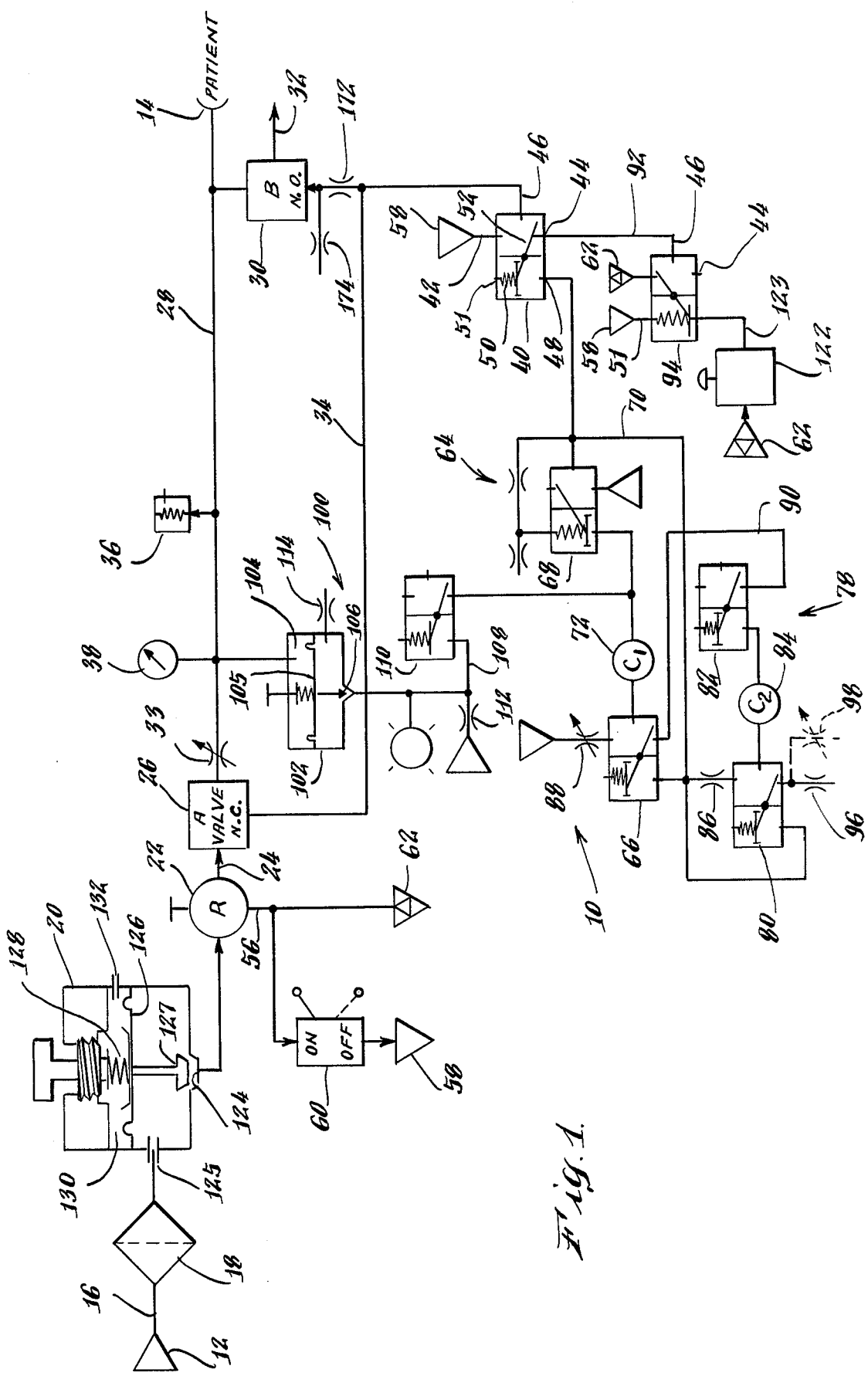
FIG. 1 is a schematic representation of a pneumatic circuit for a respirator in accordance with the invention.

With reference to FIG. 1, a pneumatic circuit 10 is shown to provide breathable gas from a supply 12 to a patient mask 14. The gas supply 12 may be any suitable gas source such as gas stored under high pressure in a cylinder or the like.

The gas is passed through a conduit 16 to a filter 18 and a safety valve 20 to a regulator 22. The regulator provides a breathable gas at the proper breathing pressure to a conduit 24 connected through an inspiratory control valve 26 to a patient supply conduit 28 connected to the patient mask 14. An exhaust or expiratory control valve 30 is shown coupling conduit 28 to atmosphere at an exhaust port 32. A flow regulator 33 is shown in series with conduit 28.

In FIG. 1 the inspiratory and expiratory control valves 26, 30 are respectively normally closed and normally open valves. This means that in the absence of an actuating pressure in conduit 34, which is coupled to the control ports of the valves, there is no inspiratory gas flow through valve 26, but a patient may exhale through valve 30. When an actuating pressure is applied to conduit 34, the operating states for valves 26, 30 are reversed.

A pressure relief valve 36 is coupled to conduit 28 to inhibit excessive gas pressure being developed at the patient mask 14 and a pressure indicator 38 is used to register the pressures in conduit 28.

In the pneumatic circuit 10 a plurality of like pneumatic bistable logic elements are employed. In these elements, for example, with reference to a preferred type of element 40, a pair of input ports 42, 44 are provided for alternate communication with an output port 46 in response to gas pressure applied to a control port 48. The element 40 normally is driven by a spring 50 into a position where a valve member 52 closes input port 42. When a gas pressure is applied to control port 48, a diaphragm coupled to the spring 50 is moved to compress spring 50 so that the operative state of the element 40 is changed to that as shown in FIG. 1 where the input port 42 is in communication with the output port 46. Note that a second control port 51 is located to enable pressurization whose effect is in opposition to that applied to main control port 48. Like numerals are employed for parts of other elements used in the pneumatic circuit 10.

Gas pressure to drive pneumatic circuit 10 is derived from a supply regulator 22 which provides gas at a suitable working pressure, of the order of 30 psi, to a supply conduit 56. In an automatic mode gas power is provided at terminal 58 through a manually selectable flow control valve switch 60. When the latter is thrown to an OFF position, the automatic mode is terminated and effectively locked out while gas power is continued to be made available at a manual gas power terminal 62. The application of gas power at various points in circuit 10 is illustrated with like symbols employed for terminals 58, 62.

The pneumatic circuit 10 includes an oscillator 64 such as is more particularly shown and described in the aforementioned copending patent application for a Pediatric Repirator bearing Ser. No. 477,194. The pneumatic oscillator 64 is formed of a pair of volume coupled bistable elements 66, 68 connected in feedback relationship by a conduit 70 to enable automatic switching of the elements. A first inspiratory control volume 72 interconnects the output port 46 of element 66 to the control port 48 of element 68 with a conduit 74. Note that the valve members 52 of all of the bistable elements are illustrated in a position corresponding to the inspiratory phase of the respirator.

During operation of oscillator 64 pneumatic respiratory phase pulses corresponding to inspiratory and expiratory respirator conditions are generated at the output port 46 of element 68. The duration of the inspiratory phase pulse is determined by the time needed to charge the volume 72 through a phase variable restrictor 76 to a pressure sufficient to switch the element 68. The duration of the expiratory phase pulse is controlled by a pneumatic network 78 formed of a pair of bistable elements 80, 82 and interconnected with a second expiratory control volume 84.

Network 78 has input port 42 and control port 48 of second volume gas charging element 80 coupled to conduit 70 to enable the second volume 84 to be charged through a restrictor 86 during the inspiratory phase.

Bistable element 80 has its control and input ports 48, 44 respectively coupled to second volume 84 and input port 44 of element 66 to discharge the first inspiratory control volume 72 just prior to the start of an inspiratory phase.

In the normal automatic operation of pneumatic circuit 10 when the inspiratory phase is just begun, the states of bistable elements 40, 66, 68, 80 and 82 are as illustrated in FIG. 1. Gas is supplied to the first volume 72 through a variable inspiration time determining restrictor 88 coupled between gas power terminal 58 and input port 42 of element 66. The gas pressure in the first volume 72, however, is not yet sufficient to switch element 68.

Hence, during inspiration, gas is supplied from output port 46 of element 68 with a sufficient pressure to maintain output element 40 in its indicated state which causes pressurization of control conduit 34 by gas power supplied at input port 42 of element 40. When conduit 34 is pressurized, expiratory control valve 30 is closed and inspiratory control valve 26 is opened to enable gas to flow to the patient mask 14 for inspiration.

During the inspiration phase the second volume 84 is charged through restrictor 86 by conduit 70. The time constants of restrictor 86, second volume 84 and variable restrictor 88 and first volume 72 are so selected that the second volume 84 achieves a sufficient pressure to switch element 82 before element 68 is switched at the end of the inspiration phase. Hence, at some time during the inspiration phase, valve member 52 of element 66 effectively closes port 44 of element 66 as illustrated in FIG. 1 with the interconnecting conduit 90.

At the end of the inspiration phase when the first volume 72 is approaching a pressure level sufficient to switch element 68, its valve member 52 seals input port 44 and establishes communication between output port 46 and atmosphere at input port 42. This quickly discharges the gas pressure in conduit 70.

The drop in pressure of conduit 70 results in a switching of elements 40, 66 and 80 to their expiration phase states. Thus the control conduit 34 is discharged through a path which includes ports 46, 44 of output element 40, conduit 92, and ports 46, 44 of a manual control element 94. The discharge of conduit 34 enables inspiration control valve 26 to return to its normally closed position and expiration control valve 30 to be opened to allow a patient to exhale.

The switching of element 80 at the end of the inspiration phase couples the second volume 84 to atmosphere through a restrictor 96. Hence, the second volume 84 is discharged at a rate which is a function of the size of restrictor 96 and the gas accumulated in second volume 84 during inspiration.

When the second volume has discharged to a low level sufficient to switch element 82, the conduit 90 effectively couples the first volume 72 to atmosphere through input port 44 and output port 46 of element 82. Element 82 thus functions to discharge the first volume 72 at a time which is effectively at the end of the expiration phase, or just prior to the start of a new inspiration phase. With the first volume 72 discharged, element 68 is switched to its inspiration state as illustrated in FIG. 1.

Since the duration of the expiration phase is a function of the size of restrictor 96, its size is preferably selected commensurate with a desired fixed inspiration to expiration time ratio. A common ratio is one to two, but others may be selected by varying the size of fixed restrictor 96 or with its replacement by a variable restrictor 98 as illustrated in phantom lines in FIG. 1. When a simple to operate respirator is desired, the variable restrictor 98 may be located in a place whose access is not readily available.

A feature of the respirator pneumatic circuit is its inclusion of an inspiratory demand sensing circuit 100. This network includes a demand sensor 102 having an input chamber 104 coupled to the patient supply conduit 28. During normal expiration the pressure in chamber 104 is sufficiently high to pressurize a spring biased diaphragm 105 and maintain a valve 106 closed. Valve 106 is coupled to a gas supply conduit 108 connected to the control port 48 of a demand bistable element 110. Hence, with normal expiration sufficient pressure is available in conduit 108 to switch demand element 110 to the state as shown in FIG. 1.

In the event a patient, during an expiratory phase, commences inhalation, sensor 102 responds by opening valve 106 and allowing pressure in conduit 108 to drop to a level sufficient to switch demand element 110 by virture of the selected sizes for restrictors 112, 114. The change in state by demand element 110 causes a quick discharge of the first volume 72 through the portion of conduit 74 connected to input port 44 of demand element 110. The discharge of the first volume 72 results in a quick termination of the expiration phase and commencement of the inspiratory phase in response to the sensed demand.

Another feature of the pneumatic circuit 10 is a manual control circuit 120 with which an operator may manually actuate control valves 26, 30. The manual control circuit 120 is actuated by first disengaging the automatic mode with the closure of valve 60 to its OFF position. This removes gas power from terminal 58 while preserving gas power on terminal 62.

Without gas power on terminal 58, the output element 40 is switched from the illustrated state in FIG. 1 to effectively couple the valve control conduit 34 to the manual control element 94. The latter may then be manually actuated with a push button controlled valve 122 coupled between gas terminal 62 and control port 48 of the element 94. Note that the application of gas terminal 58 to the auxilliary control input 51 of manual control logic element 94 automatically locks out and inhibits manual operation. This automatic lock-out arises because the pressure from valve 122 on conduit 123 is not sufficient at control port 48 to overcome the combination of the spring pressure and gas pressure applied at port 51.

Safety valve 20 is provided to close a series coupled supply port 124 in a housing in the event the gas pressure applied to entrance port 124 from source 12 drops below a predetermined level. The latter may be selected with a diaphragm 126 which is coupled to a port closing element 127 and is under pressure by a variable spring bias 128. In one side of diaphragm 126 a reference chamber 130 is exposed to atmosphere through a port 132. Hence, as long as the pressure of gas source 12 is above a limit set by the force of spring bias 128, the port 124 is open; however, when the source pressure drops, the entire pneumatic circuit is effectively disabled by closure of port 124. The force of spring bias 128 may be varied with a screw spring pressure adjustment 133 threaded into the housing for safety valve 20.

FIG. 2 shows a respirator pneumatic circuit 150 wherein an alveolar pressure measuring circuit 152 is provided to register the pressure at the patient mask 14 at the end of an inspiratory period. The pneumatic circuit 152 employs similar components as have been described with reference to FIG. 1 and are thus designated by like numerals. Circuit 152 constitutes an improvement over the end inspiratory pressure measuring circuit described and claimed in the aforementioned copending U.S. patent application for a Portable Volume Cycled Respirator filed with Ser. No. 445,758 now U.S. Pat. No. 3,910,270.

In order to measure the alveolar or airway pressure at a particular time as shown in FIG. 14 of the last mentioned patent application, a bistable element 154 is employed to momentarily couple a pressure gauge 38 to the patient supply conduit 28 connected to the gauge 38 through conduit 155. The output port 46 of element 154 is coupled to patient conduit 28 while input ports 42 connected to gauge 38 and input port 44 is closed. Hence, momentary switching of the valve member 52 of element 154 enables sampling of the pressure in patient supply conduit 28.

The generation of a pneumatic pulse at the proper time to actuate element 152 is obtained by separating the common control conduit 34 shown in FIG. 1 into two separate control lines 34–34'. Inspiratory valve 26 is actuated by a pressure developed on line 34' by an element 156 while expiratory valve 30 is actuated by a pressure produced in conduit 34 by pneumatic oscillator 64.

Conduit 74 in pneumatic oscillator 64 is shown also coupled to control port 48 of an inspiratory element 158 which has its output port 46 coupled through conduit 159 to input port 42 of the element 156 and auxiliary control port 51 of element 154. A feedback circuit is shown coupled from the output port 46 of element 158 through a restrictor 160 to auxiliary control port 51 and atmosphere through restrictor 162.

In operation, assume that the pneumatic oscillator 64 is at the beginning of an inspiratory phase and all the elements have the states as shown in FIG. 2. The conduit 159 is thus pressurized to provide gas power to actuate and open inspiratory control valve 26 while element 82 provides gas pressure to actuate and close expiratory valve 30.

The sizes of the restrictors 160, 162 and 160', 162' are so selected that the pressure developed at port 51 of element 158 is such that the latter is switched for a fixed percentage or proportion of the inspiratory phase. For example, for a time which may be from zero to about 25 percent of the time for the inspiration phase by controlling the relative pressures at ports 51 of gates 158 and 82. This may be accomplished by using variable restrictors for 160 or 162. Such timing can be appreciated with reference to FIG. 3 where an inspiratory pulse 164 is shown developed on conduit 34 by element 82. The pneumatic pulse 166 in conduit 159 is shown of shorter duration but coincident in time with the inspiratory pulse 164.

When element 158 is switched towards the end of the inspiratory period, gas pressure for actuation of inspiratory valve 26 is removed and this valve permitted to close. However, before expiration valve 30 is allowed to open, the element 154 is permitted to switch for a time period as indicated by pulse 168 in FIG. 3, and the pressure in patient conduit 28 is measured by gauge 38.

At the end of pulse 168, element 154 is returned to its illustrated state to thereby store the measured pressure in conduit 155 so that gauge 38 can continuously display the end inspiratory plateau pressure.

In order to avoid a logic conflict towards the end of the expiratory period such as at about time $t_1$ shown in FIG. 3, spring 50' in element 158 is made stronger than spring 50 of element 154. This ensures that element 158 will be switched to the state shown in FIG. 2 prior to the start of a new inspiratory cycle. One could if desired, avoid such logic conflict with additional pneumatic logic circuitry inserted in the feedback circuitry formed by restrictors 160, 162.

Note that a bypass valve 170 is provided between conduits 155 and 28 to effectively enable gauge 38 to register airway pressure throughout the operation of the respirator. The use of restrictors such as 172, 174 to operate the expiratory control valve 30 provides a suitable pressure drop for such valve actuation. When a valve 30 is selected which can operate with higher control pressures, the restrictors 172, 174 can be dispensed with.

Figure 4:
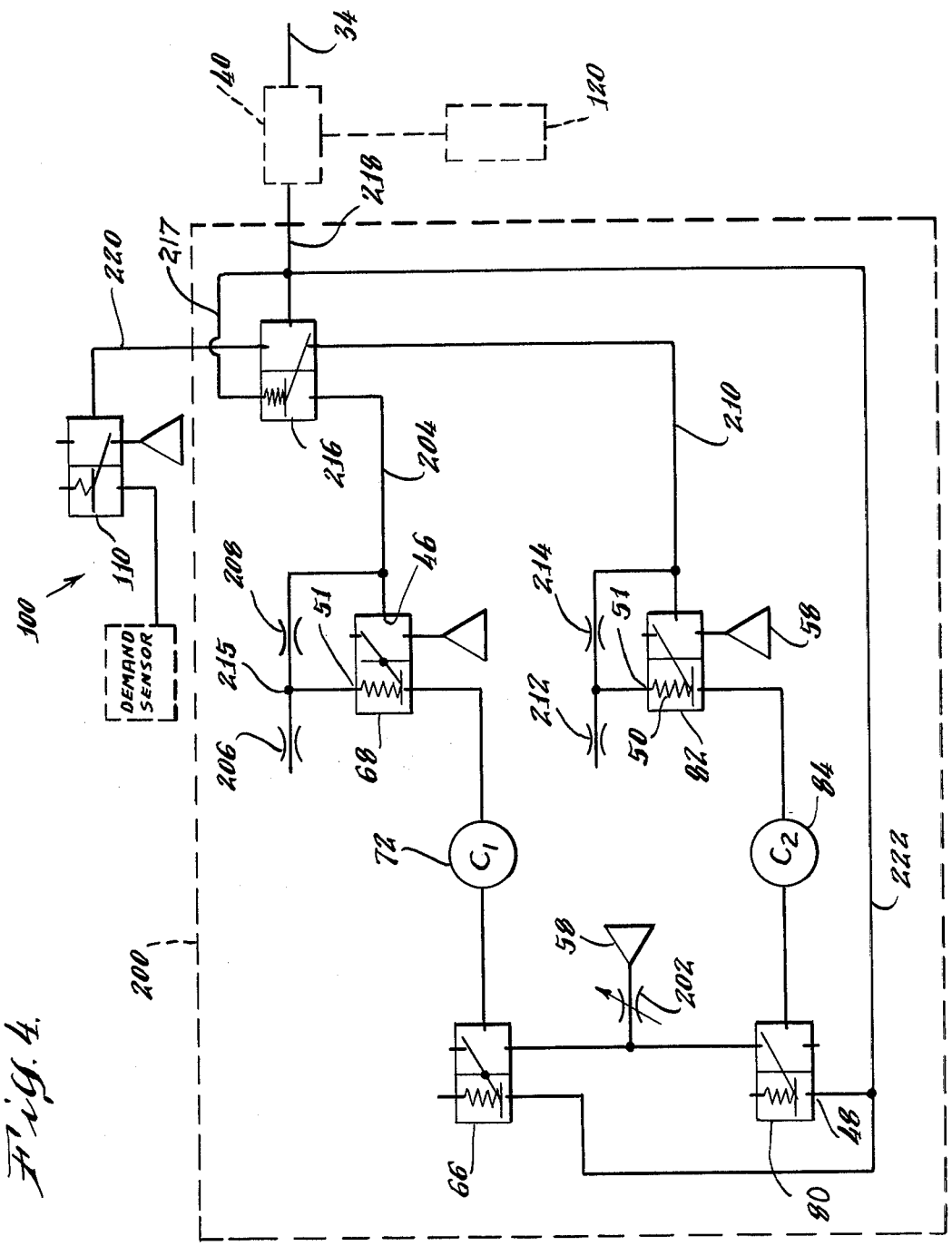
FIG. 4 is a schematic representation of an alternate pneumatic circuit for an oscillator usable in the respirator of FIG. 1.

FIG. 4 illustrates a pneumatic oscillator 200 with which a stable inspiratory to expiratory ratio can be maintained. The pneumatic oscillator 200 is formed with five logic elements instead of the four employed with the circuit 64 shown in FIG. 1. The pneumatic elements are illustrated in correspondence with a normal expiratory phase of the respirator cycle.

The oscillator 200 includes a pair of volumes 72 and 84, which are coupled to the elements in such manner that the volumes are alternately charged. The pressurization of these volumes is respectively under the control of volume pressure control logic elements 66, 80. Thus, during inspiration the first inspiratory control volume or capacitor 72 is pressurized from source 58 through a common variable restrictor 202 while the second expiratory control volume 84 is discharged by element 80. Likewise, but during expiration, the second volume is charged from source 58 through the same common variable restrictor 202 while the first volume 72 is exhausted to atmosphere by element 66.

During the inspiratory phase, an inspiratory pressure pulse is developed at the output port 46 of element 68 and conduit 204. The duration of the inspiratory pulse is made a function of the time needed for the pressure in the inspiratory control volume 72 to reach a predetermined level where element 68 is switched. Such latter level is made a function of the feedback pressure developed at the auxiliary control port 51 of element 68 by the pair of serially coupled restrictors 206, 208. When this predetermined level has been reached, the element 68 switches to its expiratory state whereby conduit 204 is exhausted to atmosphere.

In a similar manner, during the expiratory phase, an expiratory pressure pulse is developed at the output port 46 of element 82 and conduit 210. The duration of such expiratory pressure pulse is determined by the time needed for the pressure in volume 84 to reach a level selected on the relative sizes of restrictors 212, 214 connected in feedback circuit for element 82. The pressure developed at the common junction, such as 215, between the series connected restrictors 214, provides a feedback pressure on auxiliary control input 51 of element 82. This feedback pressure must be overcome in addition to the force of spring 50 by the pressure developed by volume 84 to change the state of element 82. When, at the end of an expiratory phase sufficient pressure in volume 84 occurs, element 82 is switched and the conduit 210 is exhausted to atmosphere.

A combiner element 216 is employed responsive to the outputs of elements 68, 82 on the conduits 204, 218. The combiner element 216 provides a single output on its output port 46 and conduit 218 in correspondence with the separated inspiratory and expiratory pneumatic pulses developed in conduits 204, 210.

Hence, during the inspiratory phase, pressure from source 58 is coupled through input port 44 of element 68 and conduit 204 to output conduit 218. During expiration, conduit 218 is exhausted to atmosphere along conduit 220 and the ports 42, 46 of demand element 110. The pressures developed in conduit 218, thus correspond to the inspiratory and expiratory pressure phases developed at the control port 48 of output element 40 in the pneumatic circuit of FIG. 1. The conduit 218 is thus coupled to such latter control port to provide an inspiratory and expiratory operation in the manner as described for the circuit shown in FIG. 1. Conduit 218 is also shown coupled as a feedback line 222 to control ports of elements 66, 84 for the respective initiation of inspiratory and expiratory pressures in conduits 204, 210. Since the inspiratory to expiratory (I/E) ratio is generally selected about one to two, the second volume 84 is larger than the inspiratory control volume 72 by an amount which generally corresponds to the desired I/E ratio.

With the additional element 216 and circuit arrangement of FIG. 4 a particular advantage of oscillator 200 resides in its ability to provide a stable inspiratory to expiratory ratio. A further advantage enables an immediate proper start-up of the pneumatic elements without the need to await stabilization of pressures.

Having thus described a respirator in accordance with the invention, its advantages can be appreciated. An inspiratory to expiratory time ratio can be selected suitable for most applications and employed to quickly provide respiratory aid in field situations. The respirator employs a minimum of pneumatic control circuitry whose gas consumption is kept low for enhanced efficiency and longer utilization of portable gas supplies.

What is claimed is:

1. In a respirator using a plurality of pneumatic logic elements operated by a controlled pressurized gas supply to produce a respirator cycle including a patient supply circuit means to provide a breathable gas from a supply to a patient mask through an inspiratory valve and vent exhaled gas through an expiratory valve coupled to atmosphere, wherein the pneumatic logic elements are formed with a control port, a first and a second input port, an output port and means responsive to pressure in said control port for establishing flow between the first input port and the output port and preventing flow between the second input port and the output port and responsive to a lack of pressure in said control port for establishing a gas flow between the second input port and the output port and preventing gas flow between the first input port and the output port, the improvement comprising pneumatic oscillator circuit means to provide inspiratory and expiratory breathing phases and being formed with a plurality of elements, said pneumatic oscillator circuit means including a first inspiratory control volume and a first pair of elements formed of a first volume charging element and a first volume pressure responsive element, the first volume effectively interconnecting the output port of the first volume charging element to the control port of the first volume pressure responsive element;

means for effectively coupling the output port of the first volume pressure responsive element to drive the inspiratory and expiratory valves and provide inspiratory and expiratory pressure levels to said inspiratory and expiratory valves;

the second input port of said first volume pressure responsive element and the first input port of said first volume charging element effectively connected to said controlled gas supply and the first input port of said first volume pressure responsive element being coupled to atmosphere;

a second expiratory control volume and a second pair of elements formed of a second volume charging element and a second volume pressure responsive element, said second expiratory control volume effectively interconnecting the output port of the second volume charging element to the control port of the second volume pressure responsive element;

means for coupling the control port of said second volume charging element to the control port of said first volume charging element and to the output port of the first volume pressure responsive element;

means for coupling a first input port of said first volume charging element with a supply of controlled gas at a first adjustable predetermined rate of gas flow;

means for charging the second volume through the first input port of the second volume charging element with controlled gas at a predetermined rate during one of the breathing phases and store control gas therein at a pressure level related to the duration of said one breathing phase;

second volume discharge means coupled to the second input port of said second volume charging element for discharging gas accumulated in the second volume during said one breathing phase at a discharge rate selected commensurate with that desired for the duration of the other breathing phase; and first volume discharge means coupling the second input port of said first volume charging element to the second input port of said second volume pressure responsive element for discharging the first volume when gas stored in the second volume has been discharged therefrom through the second volume discharge means for the desired duration of the other breathing phase, whereby a predetermined inspiratory to expiratory phase duration ratio is obtained by adjusting the rate of flow of control gas into the first input port of said first volume charging element.

2. The improvement as claimed in claim 1 and further including means for disabling the pneumatic oscillator circuit means and producing a manual breathing signal representative of a manually desired phase in the respiratory cycle;

an output logic element responsive to the pressure levels produced at said one output port in the first pair of elements to deliver inspiratory and expiratory pneumatic pressure levels from the pneumatic oscillator circuit means to drive the inspiratory and expiratory valves and further coupled to deliver an expiratory pressure level when said oscillator circuit means is disabled; and a manual control logic element responsive to the breathing signal and coupled to the output logic element to interrupt the expiratory pressure level therefrom for manual breathing control.

3. In a respirator using a plurality of pneumatic logic elements to produce a respirator cycle including a patient supply circuit means to provide breathable gas from a supply to a patient mask through an inspiratory valve and vent exhaled gas through an expiratory valve coupled to enable exhalation to atmosphere, the improvement comprising, a pneumatic oscillator circuit formed with a plurality of pneumatic logic elements each having a control port, an output port and first and second input ports and means responsive to pressure in said control port for establishing gas flow between the first input port and the output port and preventing gas flow between said second input port and said output port, and responsive to a lack of pressure in said control port for establishing gas flow between the second input port and the output port and preventing gas flow between the first input port and the output port;

with a first inspiratory control volume and a first pair of logic elements formed of a first volume charging element and a first volume pressure responsive element, with the first volume effectively intercoupling the output port of the first volume charging element to the control port of the first volume pressure responsive element;

said first volume charging element in the first pair including means effectively coupled to pressurize the first volume through a first input port in one operative state and providing a rapid gas discharge path for the first volume through the second input port in another operative state;

the first volume pressure responsive element in the first pair being controlled by the gas pressure level in the first volume and including means connected to the second input port to provide gas pressure level at the output port of the first volume pressure responsive element while the first volume is being pressurized;

a second expiratory control volume and a second pair of logic elements formed of a second volume charging element and a second volume pressure responsive element with the second volume effectively intercoupling the output port of the second volume charging element to the control port of the second volume pressure responsive element in said second pair of elements;

said second volume charging element including means effectively coupled to pressurize the second volume through the second input port in one operative state and providing a rapid gas discharge path through the first input port for the second volume in another operative state;

the second volume pressure responsive element in the second pair being controlled by the gas pressure level in the second volume and including means connected to the second input port to provide an expiratory determining gas pressure level at the output port of the latter element while said second volume is being presurized;

a pneumatic bistable output element having a second input port effectively coupled to the output port of said first volume pressure responsive element to provide an inspiratory gas pressure level at the output port of the output element while the first volume is being pressurized, means coupled to the first input port of the output element to establish an expiratory determining gas pressure at the output port of the output element, the output port of said second volume pressure responsive element effectively coupled to the control port of said pneumatic bistable output element to enable said latter expiratory determining gas pressure level at the output port of the latter element while said second volume is being pressurized;

means effectively coupling the output port of said pneumatic bistable output element with said inspiratory and expiratory valves whereby, said inspiratory gas pressure level closes said expiratory valve and opens said inspiratory valve and said expiratory gas pressure level opens said expiratory valve and closes said inspiratory valve;

pneumatic feedback network means for effectively coupling the output pressure level of said pneumatic bistable element to the control ports of said first and second volume charging elements in the first and second pairs to sequentially initiate said inspiratory and expiratory pressure levels.

4. The improvement as claimed in claim 3 and further including
  a common restrictor interposed between the gas supply and a first input port of said first and second volume charging elements in both the first and second pairs of elements to provide a common gas charge rate for the first and second volumes.

5. The improvement as claimed in claim 4 wherein each of the first and second volume pressure responsive elements in the first and second pairs are provided with pneumatic feedback circuits including means selected to respectively determine the pressure levels at which these latter elements are switched between their operative states respectively during inspiratory and expiratory phases of the respiratory cycle.

6. In a respirator using a plurality of pneumatic logic elements operated by a controlled pressurized gas supply to produce a respirator cycle including a patient supply circuit means to provide a breathable gas from a supply to a patient mask through an inspiratory valve and vent exhaled gas through an expiratory valve coupled to atmosphere, wherein the pneumatic logic elements are formed with a control port, a first and a second input port, an output port and means responsive to pressure in said control port for establishing flow between the first input port and the output port and preventing flow between the second input port and the output port and responsive to a lack of pressure in said control port for establishing a gas flow between the second input port and the output port and preventing gas flow between the first input port and the output port, the improvement comprising
  pneumatic oscillator circuit means to provide inspiratory and expiratory breathing phases and being formed with a plurality of said pneumatic logic elements;
  and an output port and a pair of input ports and means for establishing gas flow either between the first input port and the output port or between the second input port and the output port;
  said pneumatic oscillator circuit means including a first inspiratory control volume and a first pair of logic elements formed of a first volume charging element and a first volume pressure responsive element, means for effectively coupling the first volume between the output port of the first volume charging element and the control port of the first volume pressure responsive element, means for coupling the first input port of said first volume charging element and the second input port of said pressure responsive element to said gas supply, and pneumatic feedback network means operatively coupled to counterbias the pressure in the control port of said first volume pressure responsive element of said first pair of logic elements to generate inspiratory and expiratory pneumatic pressure levels at the output port of said latter element in the first pair;
  a second expiratory volume and a second pair of logic elements formed of a second volume charging element and a second volume pressure responsive element; means for effectively coupling the second expiratory volume between the output port of the second volume charging element and the control port of the second volume pressure responsive element;
  means responsive to a pressure level at said output port of the first volume pressure responsive element to pressurize the second volume for the same duration as the first volume and store a pressure in the second volume related to the duration of the inspiratory phase;
  second volume discharge path means including a pneumatic path between the second input port and the output port of said second volume charging element to provide a desired discharge rate for the second volume commensurate with the expiratory phase;
  first volume discharge path means including a pneumatic path between the second input port and the output port of the second volume pressure responsive element and the second input port of the first volume charging element in the first pair for discharging the first volume when the second volume pressure is at said predetermined level to achieve a predetermined inspiratory to expiratory ratio;
  demand sensor means coupled to the patient supply circuit to sense a demand for an inspiratory phase of the respiratory cycle, and a pneumatic demand control logic element having its output port coupled to atmosphere and its second input port coupled to the first volume and having its control port coupled to the demand sensor to initiate and inspiration phase when a demand occurs;
  output means for effectively coupling the output port of the first volume responsive element to the inspiratory and expiratory valves for operational drive thereof;
  manual control circuit means to provide manually actuated inspiratory and expiratory pressure levels;
  means for locking out the manual circuit when the pneumatic oscillator circuit is in operation; and
  means for coupling the manually actuated inspiratory and expiratory pressure levels to the output means to provide manual control over said inspiratory and expiratory valves when said manual circuit is operative.

7. In a respirator using a plurality of pneumatic logic elements operated by a controlled pressurized gas supply to produce a respirator cycle including a patient supply circuit means to provide a breathable gas from a supply to a patient mask through an inspiratory valve and vent exhaled gas through an expiratory valve coupled to atmosphere, wherein the pneumatic logic elements are formed with a control port, a first and a second input port, an output port and means responsive to pressure in said control port for establishing flow between the first input port and the output port and preventing flow between the second input port and the output port and responsive to a lack of pressure in said control port for establishing a gas flow between the second input port and the output port and preventing gas flow between the first input port and the output port, the improvement comprising
  an output bistable element including means effectively coupling the output port to operate the inspiratory and expiratory valves to cyclically actuate the valves for respiratory breathing cycles;
  a manual control circuit including a manually switchable pneumatic bistable element including means for manually pressurizing the control port thereof and having an output port effectively coupled to the second input port of the output bistable element to deliver pneumatic control pulses from the output port of said output bistable element in a manual control mode for the respirator;

a pneumatic oscillator formed with a first volume and a first pair of pneumatic bistable elements respectively having an output port of one of the elements and a control port of the other element effectively interconnected to each other by said first volume, means for coupling the first input port of said one element and the second input port of said other element to said gas supply, said pneumatic oscillator further including a second volume and a second pair of bistable elements respectively having an output port of one of the elements and a control port of the other element effectively interconnected to each other by said second volume, said second volume being coupled through the first input port and output port of said one element in the second pair to the output port of said other bistable element in the first pair through means for controlled pressurization of the second volume during a breathing pulse; with the second input port of said one element in the first pair coupled to the second input port of said other bistable element in the second pair for discharge of the first volume through the output port in said other element of said second pair when the second volume has been discharged to a predetermined level to achieve a predetermined ratio with respect to the duration for the inspiratory pulse;

an inspiratory demand sensing circuit including a demand sensor means coupled to the patient supply circuit means to produce a pneumatic demand signal representative thereof, a demand pneumatic bistable element having its first input port to atmosphere and having its control port coupled to the demand sensor means to receive said signal and its second input port effectively coupled to the first volume in the first pair of bistable elements to depressurize said first volume and terminate the expiratory pulse when said demand signal occurs; and means for coupling the output port of said other bistable element in the first pair of the pneumatic oscillators to the control port of said output bistable element.

8. In a respirator using a plurality of pneumatic logic elements operated by a controlled pressurized gas supply to produce a respirator cycle including a patient supply circuit means to provide a breathable gas from a supply to a patient mask through an inspiratory valve and vent exhaled gas through an expiratory valve coupled to atmosphere, wherein the pneumatic logic elements are formed with a control port, a first and a second input port, an output port and means responsive to pressure in said control port for establishing flow between the first input port and the output port and preventing flow between the second input port and the output port and responsive to a lack of pressure in said control port for establishing a gas flow between the second input port and the output port and preventing gas flow between the first input port and the output port, a pneumatic oscillator formed with a first pair of bistable elements to produce the inspiratory and expiratory pneumatic phase pulses, means effectively coupling the second input port of said first element and the first input port of said second element to said controlled gas supply and the first input port of said first element being coupled to atmosphere, said pair of elements being coupled in positive feedback relationship with a pneumatic feedback network operatively coupling the output port of the first element to the control port of the second element in the pair, a first volume effectively coupling an output port of the second element in the pair to the control port in the first element in the pair to provide and determine the duration of a pneumatic phase pulse at the output port of the first element, means for effectively coupling the output port of the first volume pressure responsive element to drive the inspiratory and expiratory valves and provide inspiratory and expiratory pressure levels to said inspiratory and expiratory valves, the improvement comprising;

an inspiratory to expiratory ratio control circuit formed with a second volume, a second volume gas charging pneumatic bistable element and a first volume discharge pneumatic bistable element, with the second volume effectively coupling the output port of the second volume gas charging element to the control port of the first volume discharge element, means for effectively coupling the output port of the first element of said first pair to the first input port of the second volume gas charging element to charge the second volume during the inspiratory phase at a predetermined rate, means for effectively coupling the output port of the first element of said first pair to the control port of the second volume gas charging element, means effectively coupled to the second input port of the second volume gas charging element to discharge the second volume at a preselected rate, the output port of said first volume discharge element coupled to atmosphere, and means for effectively coupling the second input port of the first volume discharge element to the second input port of the second element in the first pair to discharge the first volume when the second volume has been discharged to a level sufficient to cause a change of state of the first volume discharge element.

9. In a respirator using a plurality of pneumatic logic elements operated by a controlled pressurized gas supply to produce a respirator cycle including a patient supply circuit means to provide a breathable gas from a supply to a patient mask through a normally closed inspriatory valve and vent exhaled gas through a normally open expiratory valve coupled to atmosphere, wherein the pneumatic logic elements are formed with a control port, a first and a second input port, an output port and means responsive to pressure in said control port for establishing flow between the first input port and the output port and preventing flow between the second input port and the output port and responsive to a lack of pressure in said control port for establishing a gas flow between the second input port and the output port and preventing gas flow between the first input port and the output port, a pneumatic oscillator formed with a first pair of bistable elements to produce the inspriatory and expiratory pneumatic phase pulses, means effectively coupling the second input port of said first element and the first input port of said second element to said controlled gas supply and the first input port of said first element being coupled to atmosphere, said pair of elements being coupled in positive feedback relationship with a pneumatic feedback network operatively coupling the output port of the first element to the control port of the second element in the pair, a first volume effectively coupling an output port of the second element in the pair to the control port in the first element in the pair to provide and determine the duration of a pneumatic phase pulse at the output port of the first element a pneumatic bistable output element, means for coupling the output port pneumatically to both the normally closed valve and the normally open valve for valve operation; means for pneumatically coupling said output element's control port to the output port of the first element of the pair, means for pneumatically coupling the first input port of the output element to the supply of gas; and a manual control circuit having a pneumatic bistable manual element with its output port coupled to the second input port of the output element, means effectively coupling said gas supply to the first input port of said manual element, means coupled to the control port of the manual element for manually pressurizing said control port to control gas flow from the first input port of the manual element to the second input of the output element in one state of the manual element and enable discharge of gas to atmosphere from the output port of the manual element through the second input port of the manual element in another state of the manual element to establish manually controlled inspiratory and expiratory cycles.

10. The improved respirator as claimed in claim 9 and further including an expiratory control volume, means for coupling the latter volume to the output port of the first of said pair to pressurize the expiratory control volume during the inspiratory phase, and discharge means coupled to the expiratory volume and said first volume to discharge gas from the expiratory control volume at a predetermined rate to determine a time period after which the first volume is discharged to atmosphere thereby initiating another inspiratory phase whereby, the duration of the expiratory phase is defined by the discharge of the expiratory control volume and the first volume, and the duration of the inspiratory phase is determined by the charging of the first volume thereby, providing a fixed inspiratory to expiratory ratio.

* * * * *